United States Patent [19]
Rosenblum et al.

[11] Patent Number: 6,007,998
[45] Date of Patent: Dec. 28, 1999

[54] LEPTIN ASSAY

[75] Inventors: Charles I. Rosenblum, Kendall Park; Leonardus H. T. Van Der Ploeg, Scotch Plains; Sajjad A. Qureshi, Avenel; Doris F. Cully, Scotch Plains, all of N.J.; John W. Hess, Lansdale, Pa.; Michael R. Tota, Middletown, N.J.; Fang Chen, North Wales, Pa.

[73] Assignee: Merck & Co., Inc., Rahway, N.J.

[21] Appl. No.: 08/837,635

[22] Filed: Apr. 21, 1997

Related U.S. Application Data

[60] Provisional application No. 60/031,002, Nov. 15, 1996, and provisional application No. 60/016,051, Apr. 22, 1996.

[51] Int. Cl.$^6$ .......................... G01N 33/53; G01N 33/50
[52] U.S. Cl. .......................... 435/7.1; 435/7.2; 435/7.21; 435/7.8
[58] Field of Search .......................... 435/7.1, 7.2, 7.21, 435/7.8

[56] References Cited

U.S. PATENT DOCUMENTS

| | | |
|---|---|---|
| 5,401,629 | 3/1995 | Harpold et al. . |
| 5,436,128 | 7/1995 | Harpold et al. . |
| 5,643,748 | 7/1997 | Snodgrass et al. . |
| 5,698,389 | 12/1997 | de la Brousse et al. ................. 56/24.1 |

FOREIGN PATENT DOCUMENTS

| | | |
|---|---|---|
| 9629405 | 12/1990 | WIPO . |
| WO 92/02639 | 2/1992 | WIPO . |
| WO 96/05309 | 2/1996 | WIPO . |
| WO 96/38586 | 12/1996 | WIPO . |
| WO 97/19952 | 6/1997 | WIPO . |

OTHER PUBLICATIONS

He et al, *JBC* 270(48) p. 2888 7–91, 1995.
Gong et al, *JBC* 271(8) 1996, pp. 3971–3974.
De La Brousse et al, *PNAS 93*, 1996, pp. 4096–4401.
Darnell et al, *Science 264*, 1994, pp. 1415–1420.
Shki et al, *Nature 377*; 1995, pp. 591–594.
Rosenblum et al. "Functional STAT 1 and 3 signaling by the leptin receptor (OB–R); reduced expression of the rat fatty leptin receptor in transfected cells," 1996 Endocrinology 137(11):5178–5181.
Andersson et al. "Cloning, structure, and expression of the mitochondrial cytochrome P–450 sterol 26–hydroxylase, a bile biosynthetic enzyme," 1989 J. Biol. Chem. 264:8222–8229.
Barnes, W. M. "PCR amplification of up to 35–Kb DNA with high–fidelity and high–yield from lambda–bacteriophage," 1994 Proc. Natl. Acad. Sci. 91:2216–2220.
Baumann et al. "The full–length leptin receptor has signalling capabilities of interleukin 6–type cytokine receptors" 1996 Proc. Natl. Acad. Sci. USA 93:8374–8378.
Chehab et al. "Correction of the sterility defect in homozygous obese female mice by treatment with the human recombinant leptin", 1996 Nature Genetics 12:318–320.
Chen et al. "Evidence that the diabetes gene encodes the leptin receptor: Identification of a mutation in the leptin receptor gene in db/db mice" 1996 Cell 84:491–495.

Cioffi et al. "Novel B219/OB receptor isoforms:Possible role of leptin in hematopoiesis and reproduction", 1996 Nature Medicine 2:585–588.
Ghilardi et al. "Defective STAT signaling by the leptin receptor in diabetic mice" 1996 Proc. Natl. Acad. Sci. USA 93:6231–6235.
Halaas et al. "Weight–reducing effects of the plasma–protein encoded by the obese gene", 1995 Science 269:543–546.
Hodgson, J. "Receptor screening and the search for new pharmaceuticals" 1992 Bio/Technology 10:973–977.
Iida et al. "Phenotype–linked amino acid alteration in leptin receptor cDNA from zucker fatty (fa/fa) rat" 1996 Biochem. Biophys. Res. Comm. 222:19–26.
Lee et al. "Abnormal splicing of the leptin receptor in diabetic mice", 1996 Nature 379:332–335.
McKnight et al. "Transcriptional control signals of a eukaryotic protein–coding gene", 1982 Science 217:316–324.
Mellon et al. "Immortalization of hypothalamic GnRH neurons by genetically targeted tumorigenesis", 1990 Neuron 5:1–10.
Phillips et al. "Leptin receptor missense mutation in the fatty zucker rat", 1996 Nature Genetics 13:18–19.
Pine et al. "Tyrosine–phosphorylated p91 binds to a single–element in the isgf2/irf–1 promoter to mediate induction by ifn–alpha and ifn–gamma, and is likely to autoregulate the p91 gene", 1994 Embo Journal 13:158–167.
Schadlow et al. "Regulation of gene expression in PC12 cells via an activator of dual second messengers: pituitary adenylate cyclase activating polypeptide" 1992 Mol. Biol. 3:941–951.
Sims et al. "A novel interferon–inducible domain—structural and functional—analysis of the human interferon regulatory factor–I gene promoter", 1993 Molecular And Cellular Biology 13:690–702.
Tartaglia et al. "Identification and expression cloning of a leptin receptor, ob–r", 1995 Cell 83:1263–1271.
Wang et al., "A novel leptin receptor isoform in rat", 1996 FEBS Letters 392:87–90.
Zhang et al. "Positional cloning of the mouse obese gene and its human homolog", 1994 Nature 372:425–432.
Zhong et al. "Stat–3 a stat family member activated by tyrosine phosphorylation in response to epidermal growth–factor and interleukin–6", 1994 Science 264:95–98.
Zucker and Zucker "Fat accretion and growth in the rat", 1963 J. Nutrition 80:6–19.
Zucker and Zucker "Heredity obesity in the rat associated with high serum fat and cholesterol", 1962 Proc. Soc. Exp. Miol. Med. 110:164–171.
Zucker and Zucker "Fatty, a new mutation in the art", 1961 J. Heredity 52:275–278.

*Primary Examiner*—Garnette D. Draper
*Attorney, Agent, or Firm*—Anna L. Cocuzzo; Joanne M. Giesser; Jack L. Tribble

[57] ABSTRACT

A trans-activation assay for leptin is described. Leptin response elements are located proximal to a promoter, and the promoter region is operatively linked to a reporter gene. When leptin binds with the receptor, the reporter gene is transcribed.

10 Claims, 8 Drawing Sheets

```
   1 TGGGGCAATT GGGCTGACCT TTCTTATGCT GGGATGTGCC TTGGAGGACT
  51 ATGGGTGTCT ATCTCTGAAG TAAGATGACG TGTCAGAAAT TCTATGTGGT
 101 TTTGTTACAC TGGGAATTTC TGTATGTGAT AACTGCACTT AACCTGGCCT
 151 ATCCAACCTC TCCCTGGAGA TTTAAGCTGT TTTGTGCGCC ACCGAGTACA
 201 ACTGATGACT CCTTTCTCTC TCCTGCTGGA GTCCCAAACA ATACTTCGTC
 251 TTTGAAGGGG GCTTCTGAAG CACTTGTTGA AGCTAAATTT AATTCAACTG
 301 GTATCTACGT TTCTGAGTTA TCCAAAACCA TTTTCCACTG TTGCTTTGGG
 351 AATGAGCAAG GTCAAAACTG CTCCGCACTC ACAGGCAACA CTGAAGGGAA
 401 GACGCTGGCT TCAGTGGTGA AGCCTTTAGT TTTCCGCCAA CTAGGTGTAA
 451 ACTGGGACAT AGAGTGCTGG ATGAAAGGGG ACTTGACATT ATTCATCTGT
 501 CATATGGAAC CATTACTTAA GAACCCCTTC AAGAATTATG ACTCTAAGGT
 551 TCACCTTTTA TATGATCTGC CTGAAGTTAT AGATGATTTG CCTCTGCCCC
 601 CACTGAAAGA CAGCTTTCAG ACTGTCCAGT GCAACTGCAG TGTTCGGGAA
 651 TGCGAATGTC ATGTACCAGT ACCCAGAGCC AAAGTCAACT ACGCTCTTCT
 701 GATGTATTTA GAAATCACAT CTGCTGGTGT GAGTTTTCAG TCACCTCTAA
 751 TGTCACTGCA GCCCATGCTT GTTGTGAAGC CCGATCCACC GCTGGGTTTG
 801 CGTATGGAAG TCACAGATGA TGGTAATTTA AAGATTTCAT GGGACAGCCA
 851 AACAAAAGCA CCATTTCCAC TTCAATATCA GGTGAAATAT TTAGAGAATT
 901 CTACAATCGT AAGAGAGGCT GCTGAAATCG TCTCGGATAC ATCTCTGCTG
 951 GTAGACAGCG TGCTTCCTGG GTCTTCATAC GAGGTCCAGG TGAGGAGCAA
1001 GAGACTGGAT GGCTCAGGAG TCTGGAGTGA CTGGAGTTTA CCTCAACTCT
1051 TTACCACACA AGATGTCATG TATTTTCCAC CCAAAATTCT GACGAGTGTT
1101 GGATCCAATG CTTCCTTTTG CTGCATCTAC AAAAATGAGA ACCAGACTAT
1151 CTCCTCAAAA CAAATAGTTT GGTGGATGAA TCTAGCCGAG AAGATCCCCG
1201 AGACACAGTA CAACACTGTG AGTGACCACA TTAGCAAAGT CACTTTCTCC
1251 AACCTGAAAG CCACCAGACC TCGAGGGAAG TTTACCTATG ATGCAGTGTA
1301 CTGCTGCAAT GAGCAGGCAT GCCATCACCG CTACGCTGAA TTATATGTGA
1351 TCGATGTCAA TATCAATATA TCATGTGAAA CTGACGGGTA CTTAACTAAA
1401 ATGACTTGCA GATGGTCACC CAGCACAATC CAATCACTAG TGGGAAGCAC
1451 TGTGCAGTTG AGGTATCACA GGCGCAGCCT GTACTGTCCC GATAATCCAT
1501 CTATTCGTCC TACATCAGAG CTCAAAAACT GCGTCTTACA GACAGATGGC
1551 TTTTATGAAT GTGTTTTCCA GCCAATCTTT CTATTATCTG CTATACAAT
1601 GTGGATCAGG ATCAACCATT CTTTAGGTTC ACTTGACTCT CCACCAACGT
1651 GTGTCCTTCC TGACTCCGTA GTAAAACCAC TACCTCCATC TAATGTAAAA
1701 GCAGAGATTA CTATAAACAC TGGATTATTG AAAGTATCTT GGGAAAAGCC
1751 AGTCTTTCCA GAGAATAACC TTCAGTTCCA GATTCGATAT GGCTTAAATG
1801 GAAAAGAAAT ACAATGGAAG ACACACGAGG TATTCGATGC AAAATCAAAA
1851 TCGGCCAGCC TGCCAGTGTC AGATCTCTGT GCGGTCTATG TGGTACAGGT
1901 TCGCTGCCGG CGGTTGGATG GACTAGGGTA TTGGAGTAAT TGGAGCAGTC
1951 CAGCCTACAC TCTTGTCATG GATGTAAAAG TTCCTATGAG AGGGCCTGAA
2001 TTCTGGAGAA TAATGGATGG GGATATTACT AAAAAGGAGA GAAATGTCAC
```

FIG.3A

```
2051  CTTGCTTTGG AAGCCACTGA TGAAAAATGA CTCACTGTGT AGTGTGAGGA
2101  GGTATGTGGT GAAGCATCGT ACTGCCCACA ATGGGACATG GTCACAAGAT
2151  GTGGGAAATC AGACCAATCT CACTTTCCTG TGGGCAGAAT CAGCACACAC
2201  TGTTACAGTT CTGGCCATCA ATTCCATCGG TGCCTCCCTT GTGAATTTTA
2251  ACCTTACGTT CTCATGGCCC ATGAGTAAAG TGAATGCTGT GCAGTCACTC
2301  AGTGCTTATC CCCTGAGCAG CAGCTGCGTC ATCCTTTCCT GGACACTGTC
2351  ACCTAATGAT TATAGTCTGT TATATCTGGT TATTGAATGG AAGAACCTTA
2401  ATGATGATGA TGGAATGAAG TGGCTTAGAA TCCCTTCGAA TGTTAACAAG
2451  TATTATATCC ATGATAATTT TATTCCTATC GAGAAATATC AGTTTAGTCT
2501  TTACCCAGTA TTTATGGAAG GAGTTGGAAA ACCAAAGATA ATTAATGGTT
2551  TCACCAAAGA TGATATCGCC AAACAGCAAA ATGATGCAGG GCTGTATGTC
2601  ATTGTACCGA TAATTATTTC CTCTTGTGTC CTGCTGCTCG AACACTGTT
2651  AATTTCACAC CAGAGAATGA AAAAGTTGTT TTGGGACGAT GTTCCAAACC
2701  CCAAGAATTG TTCCTGGGCA CAAGGACTTA ATTTCCAAAA GCCTGAAACA
2751  TTTGAGCATC TTTTTACCAA GCATGCAGAA TCAGTGATAT TTGGTCCTCT
2801  TCTTCTGGAG CCTGAACCAG TTTCAGAAGA AATCAGTGTC GATACAGCTT
2851  GGAAAAATAA AGATGAGATG GTACCAGCAG CTATGGTCTC ACTTCTTTTG
2901  ACCACTCCAG ATTCCACAAG GGGTTCTATT TGTATCAGTG ACCAGTGTAA
2951  CAGTGCTAAC TTCTCTGGGG CTCAGAGCAC CCAGGGAACC TGTGAGGATG
3001  AGTGTCAGAG TCAACCCTCA GTTAAATATG CAACGCTGGT CAGCAACGTG
3051  AAAACAGTGG AAACTGATGA AGAGCAAGGG GCTATACATA GTTCTGTCAG
3101  CCAGTGCATC GCCAGGAAAC ATTCCCCACT GAGACAGTCT TTTTCTAGCA
3151  ACTCCTGGGA GATAGAGGCC CAGGCATTTT TCCTTTTATC AGATCATCCA
3201  CCCAATGTGA TTTCACCACA ACTTTCATTC TCAGGGTTGG ATGAGCTTTT
3251  GGAACTGGAG GGAAATTTTC CTGAAGAAAA TCACGGGGAA AAATCTGTGT
3301  ATTATCTAGG AGTCTCCTCA GGAAACAAAA GAGAGAATGA TATGCTTTTG
3351  ACTGATGAGG CAGGGGTATT GTGCCCATTC CCAGCTCACT GTCTGTTCAG
3401  TGACATCAGA ATCCTCCAGG AGAGTTGTTC ACACTTTGTA GAAAATAATT
3451  TGAATTTAGG GACCTCTGGT AAGAACTTTG TACCTTACAT GCCCCAGTTT
3501  CAATCCTGTT CCACTCACAG TCATAAGATA ATAGAAAATA AGATGTGTGA
3551  CTTAACTGTG TAATCTTGTC CAAAAACTTC CAGGTTCCAT TCCAGTAGAG
3601  TGTGTCATGT ATAATATGTT CTTTTATAGT TGTGGGTGGG AGAGAAAGCC
```

FIG.3B

```
141  CTTATGCTG
151  GGATGTGCCT TAGAGGATTA TGGGTGTACT TCTCTGAAGT AAGATGATTT
201  GTCAAAAATT CTGTGTGGTT TTGTTACATT GGGAATTTAT TTATGTGATA
251  ACTGCGTTTA ACTTGTCATA TCCAATTACT CCTTGGAGAT TTAAGTTGTC
301  TTGCATGCCA CCAAATTCAA CCTATGACTA CTTCCTTTTG CCTGCTGGAC
351  TCTCAAAGAA TACTTCAAAT TCGAATGGAC ATTATGAGAC AGCTGTTGAA
401  CCTAAGTTTA ATTCAAGTGG TACTCACTTT TCTAACTTAT CCAAAACAAC
451  TTTCCACTGT TGCTTTCGGA GTGAGCAAGA TAGAAACTGC TCCTTATGTG
501  CAGACAACAT TGAAGGAAAG ACATTTGTTT CAACAGTAAA TTCTTTAGTT
551  TTTCAACAAA TAGATGCAAA CTGGAACATA CAGTGCTGGC TAAAAGGAGA
601  CTTAAAATTA TTCATCTGTT ATGTGGAGTC ATTATTTAAG AATCTATTCA
651  GGAATTATAA CTATAAGGTC CATCTTTTAT ATGTTCTGCC TGAAGTGTTA
701  GAAGATTCAC CTCTGGTTCC CCAAAAAGGC AGTTTTCAGA TGGTTCACTG
751  CAATTGCAGT GTTCATGAAT GTTGTGAATG TCTTGTGCCT GTGCCAACAG
801  CCAAACTCAA CGACACTCTC CTTATGTGTT TGAAAATCAC ATCTGGTGGA
851  GTAATTTTCC AGTCACCTCT AATGTCAGTT CAGCCCATAA ATATGGTGAA
901  GCCTGATCCA CCATTAGGTT TGCATATGGA AATCACAGAT GATGGTAATT
951  TAAAGATTTC TTGGTCCAGC CCACCATTGG TACCATTTCC ACTTCAATAT
1001 CAAGTGAAAT ATTCAGAGAA TTCTACAACA GTTATCAGAG AAGCTGACAA
1051 GATTGTCTCA GCTACATCCC TGCTAGTAGA CAGTATACTT CCTGGGTCTT
1101 CGTATGAGGT TCAGGTGAGG GGCAAGAGAC TGGATGGCCC AGGAATCTGG
1151 AGTGACTGGA GTACTCCTCG TGTCTTTACC ACACAAGATG TCATATACTT
1201 TCCACCTAAA ATTCTGACAA GTGTTGGGTC TAATGTTTCT TTTCACTGCA
1251 TCTATAAGAA GGAAAACAAG ATTGTTCCCT CAAAAGAGAT TGTTTGGTGG
1301 ATGAATTTAG CTGAGAAAAT TCCTCAAAGC CAGTATGATG TTGTGAGTGA
1351 TCATGTTAGC AAAGTTACTT TTTTCAATCT GAATGAAACC AAACCTCGAG
1401 GAAAGTTTAC CTATGATGCA GTGTACTGCT GCAATGAACA TGAATGCCAT
1451 CATCGCTATG CTGAATTATA TGTGATTGAT GTCAATATCA ATATCTCATG
1501 TGAAACTGAT GGGTACTTAA CTAAAATGAC TTGCAGATGG TCAACCAGTA
1551 CAATCCAGTC ACTTGCGGAA AGCACTTTGC AATTGAGGTA TCATAGGAGC
1601 AGCCTTTACT GTTCTGATAT TCCATCTATT CATCCCATAT CTGAGCCCAA
1651 AGATTGCTAT TTGCAGAGTG ATGGTTTTTA TGAATGCATT TTCCAGCCAA
1701 TCTTCCTATT ATCTGGCTAC ACAATGTGGA TTAGGATCAA TCACTCTCTA
1751 GGTTCACTTG ACTCTCCACC AACATGTGTC CTTCCTGATT CTGTGGTGAA
1801 GCCACTGCCT CCATCCAGTG TGAAAGCAGA AATTACTATA AACATTGGAT
1851 TATTGAAAAT ATCTTGGGAA AAGCCAGTCT TTCCAGAGAA TAACCTTCAA
1901 TTCCAGATTC GCTATGGTTT AAGTGGAAAA GAAGTACAAT GGAAGATGTA
1951 TGAGGTTTAT GATGCAAAAT CAAAATCTGT CAGTCTCCCA GTTCCAGACT
2001 TGTGTGCAGT CTATGCTGTT CAGGTGCGCT GTAAGAGGCT AGATGGACTG
2051 GGATATTGGA GTAATTGGAG CAATCCAGCC TACACAGTTG TCATGGATAT
2101 AAAAGTTCCT ATGAGAGGAC CTGAATTTTG GAGAATAATT AATGGAGATA
```

FIG.4A

```
2151  CTATGAAAAA GGAGAAAAAT GTCACTTTAC TTTGGAAGCC CCTGATGAAA
2201  AATGACTCAT TGTGCAGTGT TCAGAGATAT GTGATAAACC ATCATACTTC
2251  CTGCAATGGA ACATGGTCAG AAGATGTGGG AAATCACACG AAATTCACTT
2301  TCCTGTGGAC AGAGCAAGCA CATACTGTTA CGGTTCTGGC CATCAATTCA
2351  ATTGGTGCTT CTGTTGCAAA TTTTAATTTA ACCTTTTCAT GGCCTATGAG
2401  CAAAGTAAAT ATCGTGCAGT CACTCAGTGC TTATCCTTTA AACAGCAGTT
2451  GTGTGATTGT TTCCTGGATA CTATCACCCA GTGATTACAA GCTAATGTAT
2501  TTTATTATTG AGTGGAAAAA TCTTAATGAA GATGGTGAAA TAAAATGGCT
2551  TAGAATCTCT TCATCTGTTA AGAAGTATTA TATCCATGAT CATTTTATCC
2601  CCATTGAGAA GTACCAGTTC AGTCTTTACC AATATTTAT GGAAGGAGTG
2651  GGAAAACCAA AGATAATTAA TAGTTTCACT CAAGATGATA TTGAAAAACA
2701  CCAGAGTGAT GCAGGTTTAT ATGTAATTGT GCCAGTAATT ATTTCCTCTT
2751  CCATCTTATT GCTTGGAACA TTATTAATAT CACACCAAAG AATGAAAAAG
2801  CTATTTTGGG AAGATGTTCC GAACCCCAAG AATTGTTCCT GGGCACAAGG
2851  ACTTAATTTT CAGAAGCCAG AAACGTTTGA GCATCTTTTT ATCAAGCATA
2901  CAGCATCAGT GACATGTGGT CCTCTTCTTT TGGAGCCTGA AACAATTTCA
2951  GAAGATATCA GTGTTGATAC ATCATGGAAA AATAAAGATG AGATGATGCC
3001  AACAACTGTG GTCTCTCTAC TTTCAACAAC AGATCTTGAA AAGGGTTCTG
3051  TTTGTATTAG TGACCAGTTC AACAGTGTTA ACTTCTCTGA GGCTGAGGGT
3101  ACTGAGGTAA CCTATGAGGC CGAAAGCCAG AGACAACCCT TTGTTAAATA
3151  CGCCACGCTG ATCAGCAACT CTAAACCAAG TGAAACTGGT GAAGAACAAG
3201  GGCTTATAAA TAGTTCAGTC ACCAAGTGCT TCTCTAGCAA AAATTCTCCG
3251  TTGAAGGATT CTTTCTCTAA TAGCTCATGG GAGATAGAGG CCCAGGCATT
3301  TTTTATATTA TCAGATCAGC ATCCCAACAT AATTTCACCA CACCTCACAT
3351  TCTCAGAAGG ATTGGATGAA CTTTTGAAAT TGGAGGGAAA TTTCCCTGAA
3401  GAAAATAATG ATAAAAGTC TATCTATTAT TTAGGGGTCA CCTCAATCAA
3451  AAAGAGAGAG AGTGGTGTGC TTTTGACTGA CAAGTCAAGG GTATCGTGCC
3501  CATTCCCAGC CCCCTGTTTA TTCACGGACA TCAGAGTTCT CCAGGACAGT
3551  TGCTCACACT TTGTAGAAAA TAATATCAAC TTAGGAACTT CTAGTAAGAA
3601  GACTTTTGCA TCTTACATGC CTCAATTCCA AACTTGTTCT ACTCAGACTC
3651  ATAAGATCAT GGAAAACAAG ATGTGTGACC TAACTGTGTA ATTTCACTGA
3701  AGAAACCTTC AGATTTGTGT TATAATGGGT AATATAAAGT GTAATAGATT
3751  ATAGTTGTGG GTGGGAGAGA
```

FIG.4B

```
   1  TGGGGCAATT GGGCTGACCT TTCTTATGCT GGGATGTGCC TTGGAGGACT
  51  ATGGGTGTCT ATCTCTGAAG TAAGATGACG TGTCAGAAAT TCTATGTGGT
 101  TTTGTTACAC TGGGAATTTC TGTATGTGAT AACTGCACTT AACCTGGCCT
 151  ATCCAACCTC TCCCTGGAGA TTTAAGCTGT TTTGTGCGCC ACCGAGTACA
 201  ACTGATGACT CCTTTCTCTC TCCTGCTGGA GTCCCAAACA ATACTTCGTC
 251  TTTGAAGGGG GCTTCTGAAG CACTTGTTGA AGCTAAATTT AATTCAACTG
 301  GTATCTACGT TTCTGAGTTA TCCAAAACCA TTTTCCACTG TTGCTTTGGG
 351  AATGAGCAAG GTCAAAACTG CTCCGCACTC ACAGGCAACA CTGAAGGGAA
 401  GACGCTGGCT TCAGTGGTGA AGCCTTTAGT TTTCCGCCAA CTAGGTGTAA
 451  ACTGGGACAT AGAGTGCTGG ATGAAAGGGG ACTTGACATT ATTCATCTGT
 501  CATATGGAAC CATTACTTAA GAACCCCTTC AAGAATTATG ACTCTAAGGT
 551  TCACCTTTTA TATGATCTGC CTGAAGTTAT AGATGATTTG CCTCTGCCCC
 601  CACTGAAAGA CAGCTTTCAG ACTGTCCAGT GCAACTGCAG TGTTCGGGAA
 651  TGCGAATGTC ATGTACCAGT ACCCAGAGCC AAAGTCAACT ACGCTCTTCT
 701  GATGTATTTA GAAATCACAT CTGCTGGTGT GAGTTTCAG TCACCTCTAA
 751  TGTCACTGCA GCCCATGCTT GTTGTGAAGC CTGGAGTTTA CCTCAACTCT
 801  CGTATGGAAG TCACAGATGA TGGTAATTTA AAGATTTCAT GGGACAGCCA
 851  AACAAAAGCA CCATTTCCAC TTCAATATCC GGTGAAATAT TTAGAGAATT
 901  CTACAATCGT AAGAGAGGCT GCTGAAATCG TCTCGGATAC ATCTCTGCTG
 951  GTAGACAGCG TGCTTCCTGG CTGTTCATAC GAGGTCCAGG TGAGGAGCAA
1001  GAGACTGGAT GGCTCAGGAG TCTGGAGTGA CTGGAGTTTA CCTCAACTCT
1051  TTACCACACA AGATGTCATG TATTTTCCAC CCAAAATTCT GACGAGTGTT
1101  GGATCCAATG CTTCCTTTTG CTGCATCTAC AAAAATGAGA ACCAGACTAT
1151  CTCCTCAAAA CAAATAGTTT GGTGGATGAA TCTAGCCGAG AAGATCCCCG
1201  AGACACAGTA CAACACTGTG AGTGACCACA TTAGCAAAGT CACTTTCTCC
1251  AACCTGAAAG CCACCAGACC TCGAGGGAAG TTTACCTATG ATGCAGTGTA
1301  CTGCTGCAAT GAGCAGGCAT GCCATCACCG CTACGCTGAA TTATATGTGA
1351  TCGATGTCAA TATCAATATA TCATGTGAAA CTGACGGGTA CTTAACTAAA
1401  ATGACTTGCA GATGGTCACC CAGCACAATC CAATCACTAG TGGGAAGCAC
1451  TGTGCAGTTG AGGTATCACA GGCGCAGCCT GTACTGTCCC GATAATCCAT
1501  CTATTCGTCC TACATCAGAG CTCAAAAACT GCGTCTTACA GACAGATGGC
1551  TTTTATGAAT GTGTTTTCCA GCCAATCTTT CTATTATCTG GCTATACAAT
1601  GTGGATCAGG ATCAACCATT CTTTAGGTTC ACTTGACTCT CCACCAACGT
1651  GTGTCCTTCC TGACTCCGTA GTAAAACCAC TACCTCCATC TAATGTAAAA
1701  GCAGAGATTA CTATAAACAC TGGATTATTG AAAGTATCTT GGGAAAAGCC
1751  AGTCTTTCCA GAGAATAACC TTCAGTTCCA GATTCGATAT GGCTTAAATG
1801  GAAAAGAAAT ACAATGGAAG ACACACGAGG TATTCGATGC AAAATCAAAA
1851  TCGGCCAGCC TGCCAGTGTC AGATCTCTGT GCGGTCTATG TGGTACAGGT
1901  TCGCTGCCGG CGGTTGGATG GACTAGGGTA TTGGAGTAAT TGGAGCAGTC
1951  CAGCCTACAC TCTTGTCATG GATGTAAAAG TTCCTATGAG AGGGCCTGAA
2001  TTCTGGAGAA TAATGGATGG GGATATTACT AAAAAGGAGA GAAATGTCAC
2051  CTTGCTTTGG AAGCCACTGA TGAAAAATGA CTCACTGTGT AGTGTGAGGA
```

FIG.5A

```
2101  GGTATGTGGT GAAGCATCGT ACTGCCCACA ATGGGACATG GTCACAAGAT
2151  GTGGGAAATC AGACCAATCT CACTTTCCTG TGGGCAGAAT CAGCACACAC
2201  TGTTACAGTT CTGGCCATCA ATTCCATCGG TGCCTCCCTT GTGAATTTTA
2251  ACCTTACGTT CTCATGGCCC ATGAGTAAAG TGAATGCTGT GCAGTCACTC
2301  AGTGCTTATC CCCTGAGCAG CAGCTGCGTC ATCCTTTCCT GGACACTGTC
2351  ACCTAATGAT TATAGTCTGT TATATCTGGT TATTGAATGG AAGAACCTTA
2401  ATGATGATGA TGGAATGAAG TGGCTTAGAA TCCCTTCGAA TGTTAACAAG
2451  TATTATATCC ATGATAATTT TATTCCTATC GAGAAATATC AGTTTAGTCT
2501  TTACCCAGTA TTTATGGAAG GAGTTGGAAA ACCAAAGATA ATTAATGGTT
2551  TCACCAAAGA TGATATCGCC AAACAGCAAA ATGATGCAGG GCTGTATGTC
2601  ATTGTACCGA TAATTATTTC CTCTTGTGTC CTGCTGCTCG GAACACTGTT
2651  AATTTCACAC CAGAGAATGA AAAAGTTGTT TTGGGACGAT GTTCCAAACC
2701  CCAAGAATTG TTCCTGGGCA CAAGGACTTA ATTTCCAAAA GCCTGAAACA
2751  TTTGAGCATC TTTTTACCAA GCATGCAGAA TCAGTGATAT TTGGTCCTCT
2801  TCTTCTGGAG CCTGAACCAG TTTCAGAAGA AATCAGTGTC GATACAGCTT
2851  GGAAAAATAA AGATGAGATG GTACCAGCAG CTATGGTCTC ACTTCTTTTG
2901  ACCACTCCAG ATTCCACAAG GGGTTCTATT TGTATCAGTG ACCAGTGTAA
2951  CAGTGCTAAC TTCTCTGGGG CTCAGAGCAC CCAGGGAACC TGTGAGGATG
3001  AGTGTCAGAG TCAACCCTCA GTTAAATATG CAACGCTGGT CAGCAACGTG
3051  AAAACAGTGG AAACTGATGA AGAGCAAGGG CTATACATA GTTCTGTCAG
3101  CCAGTGCATC GCCAGGAAAC ATTCCCCACT GAGACAGTCT TTTTCTAGCA
3151  ACTCCTGGGA GATAGAGGCC CAGGCATTTT TCCTTTTATC AGATCATCCA
3201  CCCAATGTGA TTTCACCACA ACTTTCATTC TCAGGGTTGG ATGAGCTTTT
3251  GGAACTGGAG GGAAATTTTC CTGAAGAAAA TCACGGGGAA AAATCTGTGT
3301  ATTATCTAGG AGTCTCCTCA GGAAACAAAA GAGAGAATGA TATGCTTTTG
3351  ACTGATGAGG CAGGGGTATT GTGCCCATTC CCAGCTCACT GTCTGTTCAG
3401  TGACATCAGA ATCCTCCAGG AGAGTTGTTC ACACTTTGTA GAAAATAATT
3451  TGAATTTAGG GACCTCTGGT AAGAACTTTG TACCTTACAT GCCCCAGTTT
3501  CAATCCTGTT CCACTCACAG TCATAAGATA ATAGAAAATA AGATGTGTGA
3551  CTTAACTGTG TAATCTTGTC CAAAAACTTC CAGGTTCCAT TCCAGTAGAG
3601  TGTGTCATGT ATAATATGTT CTTTTATAGT TGTGGGTGGG AGAGAAAGCC
```

FIG.5B

LEPTIN ASSAY

CROSS-REFERENCE TO RELATED APPLICATIONS

This application claims priority from provisional application 60/031,002 filed Nov. 15, 1996, and provisional application 60/016,051 filed Apr. 22, 1996.

STATEMENT REGARDING FEDERALLY-SPONSORED R&D

Not Applicable.

REFERENCE TO MICROFICHE APPENDIX

Not Applicable.

FIELD OF THE INVENTION

This invention relates to an assay for determining the presence of compounds which bind to a leptin receptor. This invention also relates to an assay for quantifying the amount of a leptin receptor binding agent present in a sample.

BACKGROUND OF THE INVENTION

Leptin is a product of the Ob gene (Zhang et al., 1995 Nature 372:425–432). In its absence, mice develop extreme obesity resembling morbid obesity of humans. They also develop diabetes resembling human type II diabetes (Zhang et al., supra), and become infertile (Chehab et al., 1996 Nature Genetics 12:318–320). Restoration of leptin reverses these pathologies.

Currently, the only manner in which preparations of recombinant leptin can be assayed is by injection of large quantities into ob/ob mice (Campfield, 1995 Science 269:546–549; Rentsch 1995, Biochem Biophys Res Comm 214:131–136). Leptin activity is assessed based upon depression of feed intake and is highly variable among individuals. No mutually agreed upon standard of leptin activity exists. Therefore, a rapid, accurate assay for leptin bioactivity which utilizes small amounts of leptin would be desirable.

DETAILED DESCRIPTION OF THE INVENTION

This invention relates to a method for determining if a leptin receptor binding compound is present in a sample comprising:

contacting the sample with a cell which comprises a) nucleic acids comprising a promoter region, said promoter region comprising a promoter and at least one leptin response element; said promoter region operatively linked to a reporter gene; and b) nucleic acids encoding a leptin receptor; and determining if transcription of the reporter gene occurs.

BRIEF DESCRIPTION OF THE DRAWINGS

FIG. 3A–B is the DNA sequence for lean rat Ob-r.

FIG. 4A–B is the DNA sequence for human Ob-r which has been placed in the pCMV4 vector. The Gen Bank accession number for human Ob-r is U43168. Nucleotides 141-37-7-0 are used in pCMV4-Ob-4.

FIG. 5A–B is the DNA sequence for fatty rat Ob-r.

Figure 1:
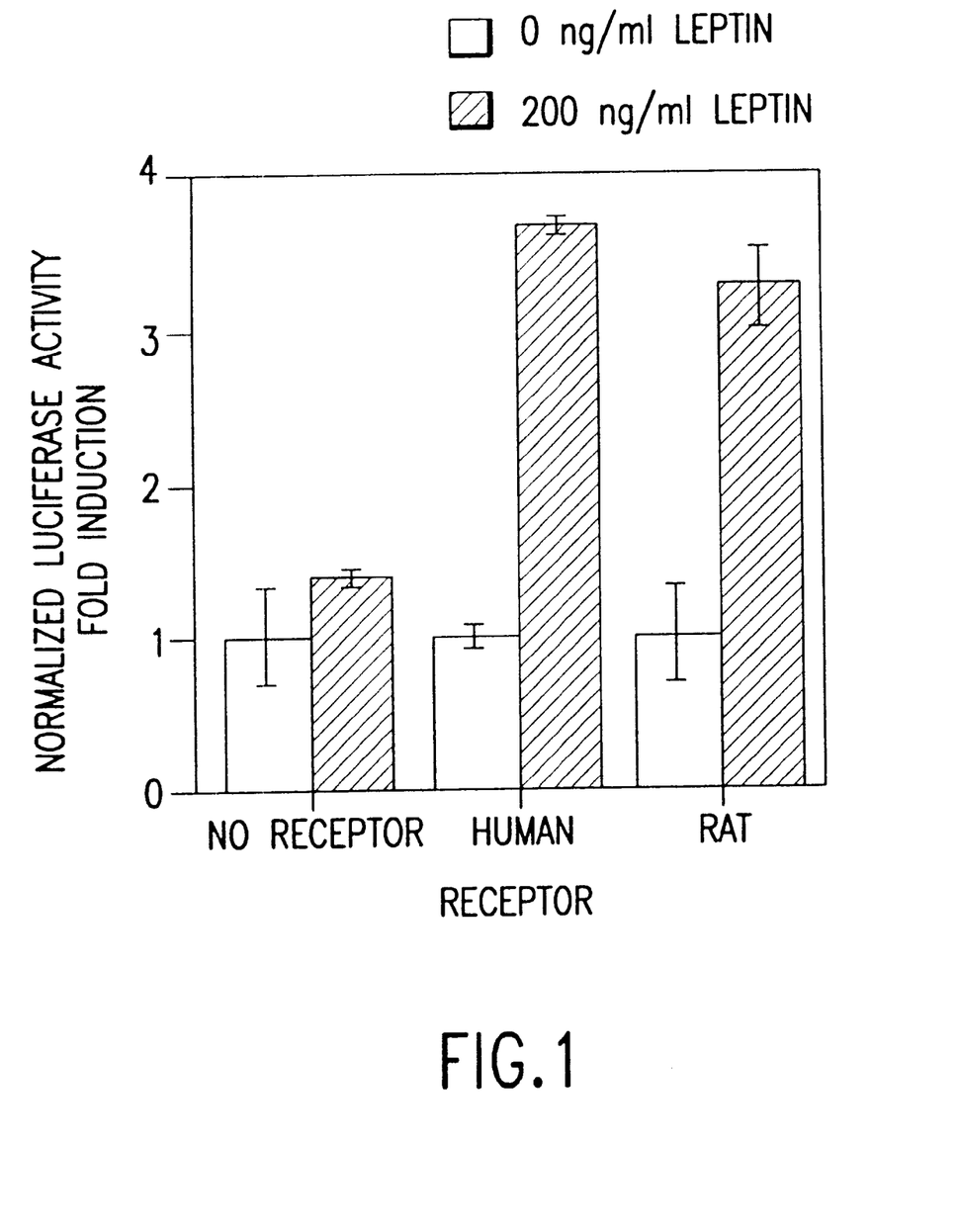
FIG. 1 is a graph showing functional assay of leptin using GT1–7 cells. Cells were either: mock transfected with respect to Ob-r, transfected with lean rat Ob-r cDNA, or transfected human Ob-r cDNA and showed induction of luciferase activity in cell expressing Ob-r treated with leptin.
Figure 2:
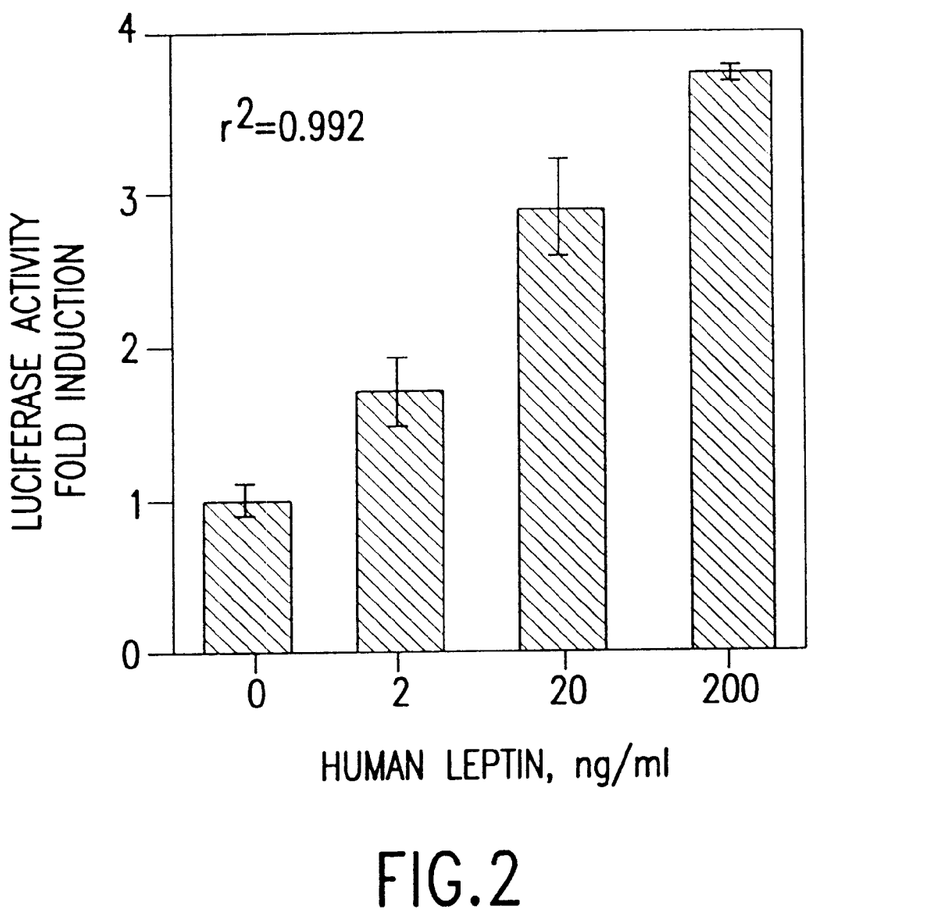
FIG. 2 is a graph showing that cells respond in a dose-dependent manner to the addition of leptin as determined by increase in luciferase activity. GT1–7 cells were transiently transfected with human Ob-r and treated with various amounts of human leptin.

As used throughout the specification and claims, the following definition shall apply:

"Leptin receptor binding compound" means a compound which binds to a leptin receptor.

"Leptin mimetic" means a compound other than leptin which binds to a leptin receptor and triggers a cascade of intracellular reactions which ultimately results in transcription of DNA under the control of leptin response elements.

"Leptin response elements" means DNA sequences located within a promoter region which are responsive to a leptin receptor binding event, and in the presence of such an event, allow for transcription of the DNA under the control of the promoter.

"Promoter region" means DNA located upstream of a protein or peptide encoding sequence, and includes at least one response element.

"Promoter" includes full length promoters, minimal promoters and promoters which are less than full length, but include more nucleic acids than minimal promoters.

"Ob-r" means Ob-receptor.

"Full length Ob-r" means a complete protein, such as the one described in Tartaglia et al., 1995, Cell 83:1263–1271.

"Ob-r(a)" means Ob-receptor short form, having a shorter intracellular sequence than the longer full length form as defined in Tartaglia et al., 1995 Cell 83:1263–1271.

One aspect of this invention is a cellular "trans" activation assay which can determine if a particular compound can bind to a leptin receptor. In general, the binding of a ligand to its membrane-bound receptor initiates an intracellular cascade of signals. Ultimately, a specific transcriptional control element is activated, leading to the transcription of DNA. It has been found, in accordance with this invention, that the binding of native leptin with its native leptin receptor initiates a cascade which activates leptin response elements, leading to the transcription of DNA. One such leptin response element which has been identified in accordance with this invention is an IRF-1 derived gamma-interferon activation sequence. IRF-1 derived activation sequences have been described in the art (Pine et al., 1994 EMBO J. 13:158–167) but their responsiveness to leptin—leptin receptor binding events has been heretofore unknown.

This discovery of a leptin response element has allowed for the design of various assays which form the basis of this invention. A promoter region is constructed which contains a promoter of choice and one or more leptin response elements. The promoter region may be a hybrid promoter region, i.e. contain a promoter and one or more response elements which do not naturally occur together, or it may be a naturally occurring promoter region with one or more associated response elements. In a preferred embodiment the promoter is a well-characterized promoter, such as the herpes simplex virus thymidine kinase promoter, but any promoter which is known to function in the host cell chosen may be used. It is also preferred that the promoter be a minimal promoter, so that there are no transcriptional control sequences which may influence the activity of the leptin response element(s).

The leptin-response element is preferably placed proximal to the promoter. Intervening sequences may be present between the leptin response element and the promoter, provided they do not interfere with the functioning of the leptin response element.

In accordance with this invention, a suitable leptin response element is an IRF-1 derived gamma interferon activation sequence 5'-CTGATTTCCC CGAAATGACG-3' (SEQ. ID NO. 1). In a preferred embodiment, the promoter region comprises a plurality of IRF-1 derived gamma interferon activation sequences; and more preferably it comprises at least three such sequences. When a plurality of leptin response elements are present, they are preferably joined in tandem. However, there may be interviewing sequences present provided they do not interfere with the functioning of the leptin response elements.

Other cytokine activation sequences, known in the art may also be used in place of or in addition to the IRF-1 derived gamma interferon activation sequence. These include the STAT binding sequences.

In order to detect transcription which occurs as a result of the leptin—leptin receptor binding, it is preferred to operatively link a reporter gene to the promoter region which contains at least one leptin response element. A reporter gene may be any gene which encodes a peptide which is easily detected, or otherwise allows for easy detection of transcription or translation. It generally encodes a protein which does not naturally occur in the host cell or only is produced in small amounts by the host cell. Examples of well known reporter genes include: chloramphenicol acetyl transferase (CAT), green fluorescent protein (GFP), luciferase (either bacterial or firefly), and other enzyme-based detection systems such as $\beta$-galactosidase, alkaline phosphatase, and the like. In a particularly preferred embodiment, luciferase is a reporter gene. In alternative embodiments, the mRNA transcribed from the reporter gene DNA may be measured rather than the translation product.

The reporter gene construct, which comprises a) a promoter region which comprises a promoter and at least one leptin response element and b) the reporter gene (operatively linked to the promoter region) forms yet another aspect of this invention. It is preferably placed in an appropriate vector and in used to transfect a host cell. This vector comprises yet another aspect of the invention. The vector may be any known vector, including plasmids, cosmids and viral vectors which can function in a chosen host cell.

The host cell may be any cell or cell line which is conveniently cultured. In general, a preferred host cell will be eukaryotic, preferably mammalian, and in particularly preferred embodiments it is a mouse hypothalamic cell (such as GT1–7, NLT or Gn11), a mammalian neuroblastoma cell line, human brain neuron (SK-NMC or SK-N-BE2) mouse fibroblast cell lines such as NIH/3T3 (ATCC CRL 1658) or L (ATCC CCL 1), Chinese hamster ovary CHO-K1 cells (ATCC CCL 61) human embryonic kidney-derived 293 cells (ATCC CRL 1573), or CDS cells.

The host cell should either have an abundance of leptin receptors on its surface or it can be transformed to express an abundance of leptin receptors on its surface, the latter situation being the preferred one.

Any native or modified leptin receptor may be used; human and rodent ones are preferred. Nucleic acids encoding human leptin receptors have been described (Tartaglia et al., 1995 *Cell* 83:1263–1271, which is hereby incorporated by reference) and are shown in FIG. 4. Mouse receptor genes can also be used, especially the position 26 to 2775, based on the sequence given in Gen Bank. Nucleic acids encoding leptin receptors from wild-type rats, fatty rats (fa/fa genotype) (shown in FIG. 3) and rats heterozygous for the ob receptor gene (shown in FIG. 5) are described in co-pending U.S. application Ser. Nos. 60/146,928 and 60/013,969, Attorney Docket Nos. 19642PV filed Feb. 22, 1996 and 19642PV2, filed Mar. 22, 1996, both of which are hereby incorporated by reference.

By transfecting cells with various leptin receptors individually or in combination, the biological response of receptors from different sources can be studied and compared. Also, leptin receptors containing particular desired mutations can be constructed according to known molecular biological techniques and the structure and function of the mutants can be studies using the assay of this invention. The Ob-R has been transiently expressed in a number of different cell lines, including mouse. For example, Ob-r(a) is inactive while Ob-r is active. However, the activity of Ob-r is suppressed in the presence of Ob-r(a) in a dose-dependent manner.

Another aspect of this invention is a set of vectors suitable for transfecting a host cell so that it can be used in the assays of this invention. The set of vectors comprises a first vector which contains a leptin receptor construct. The leptin receptor construct includes nucleic acids encoding a desired leptin receptor or mutated form of the receptor. It may be under the control of its native promoter or any other desired heterologous promoter. Optionally it may also contain other expression-control elements, such as enhancers and sequences which assist in expressing the receptor on the membrane.

The set of vectors also comprises a second vector comprising the reporter gene construct described previously.

In a preferred assay of this invention, compounds which are suspected of being leptin receptor ligands can be assayed. In this embodiment, cells which express a leptin receptor (either naturally or due to recombinant methods) are transfected with the reporter gene construct described previously and may be transfected with a leptin receptor construct, if the cell does not naturally express an abundance of the leptin receptor. The putative leptin receptor ligand is placed in contact with the transfected cells, and the presence of the reporter gene transcription or translation product is detected. This may be compared to the amount of transcription or translation measured in a control assay, where an identically transfected cell is placed in contact with leptin. A further advantage of the assay of this invention is that it is dose-responsive; i.e. as more leptin ligand-leptin receptor binding occurs, transcription and/or translation of reporter gene increases, and therefore allows for a quantitative determination of leptin receptor binding activity.

A counterscreen may also be employed as a part of this assay. In the counterscreen, a second cell of the same cell type is transfected with the reporter gene construct described previously, but is not transfected with the leptin receptor gene construct. The putative leptin receptor ligand is placed in contact with the transfected cells and the presence of of the reporter gene transcription or translation is detected. Those putative leptin receptor ligands which activate the reporter gene construct only in the presence of leptin receptor are determined to be specific leptin agonists.

Using this embodiment of the assay, leptin agonists and antagonists may be identified. A leptin agonist is a compound which binds to the leptin receptor, such as a leptin mimetic, and produces a cellular response which is at least about equivalent to that of leptin, and which may be greater than that of leptin. Such compounds would be useful in situations where leptin insufficiency causes obesity, diabetes or infertility.

Also using this embodiment of the assay, leptin antagonists may be identified. A leptin antagonist is a compound which can bind to the leptin receptor, but produces a lesser response than that of native leptin. Such compounds would be useful in the treatment of anorexia and cachexia.

In another aspect of this invention, novel leptin response elements can be identified by inserting various putative leptin response elements proximal to a promoter which controls the transcription of a reporter gene. A cell transfected with this construct and expressing natural or recombinant leptin receptors is contacted with leptin. The resulting transcription of the reporter gene is compared with that which occurs when the leptin response element is an IRF-1 derived gamma interferon activation sequence. Novel leptin response elements which are identified using this assay form yet another aspect of this invention.

In another embodiment of this invention, the potency of a leptin preparation can be determined, and quantified. In this embodiment, the leptin-containing preparation is contacted with the cell containing the reporter gene construct and which is expressing leptin receptors (either recombinant or native). The amount of transcription and/or translation of the reporter gene is measured and is compared to that obtained using preparations of known potency.

In yet another aspect of this invention, the biological activity of various leptin receptors can be studied and compared. In this embodiment, a first cell is transfected with a reporter gene construct and a first leptin receptor. The first leptin receptor can be any leptin receptor or variant or mutant whose activity is to be determined. The first cell is put into contact with leptin and the reporter gene transcription or translation is measured. This amount is compared to that obtained under the same assay conditions using a second leptin receptor whose activity is known or is otherwise to be used as a reference. With this embodiment, Ob-r(a) is found to be inactive while Ob-r is active. When the two receptors are co-expressed in the same cell, the activity of Ob-r is suppressed by Ob-r(a).

In yet another embodiment of this invention, the structure of Ob receptors can be studied. The Ob-receptor belongs to the cytokine family of receptors. Many cytokine receptors have a ligand binding subunit and a signalling subunit. A higher affinity has been observed in the presence of a signalling subunit. In order to investigate whether the Ob-r receptor had such signalling subunits, common cytokine receptor signalling subunits such as gp130, KH97 and IL2R-$\gamma$ the transactivation assay of this invention may be used. Leptin-induced response of the reporter gene was measured in the presence and absence of co-expressed gp130, KH97 and IL2R-$\gamma$. While there was no significant change when gp130 or IL2R-$\gamma$ was present, KH97 suppressed the leptin-induced response, but could be partially reversed by JAK2 co-expression.

In similar experiments, the short form of the receptor, Ob-R(a) was co-expressed with the full length Ob-R in the presence of STAT. The short Ob-R(a) contains a JAK binding site, but lacks the STAT binding site. Ob-R(a) was found to suppress the leptin response.

The following non-limiting Examples are presented to better illustrate the invention.

EXAMPLE 1

Vector Construction

AH32, an expression vector transactivated by leptin, was constructed as follows. Two complimentary oligonucleotides containing the Stat Binding Element (SBE) from the IRF-1 gene (Sims et al., 1993 *Mol Cell Biol.* 13:690–702; and Pine et al., 1994 *EMBO J.* 13:158–167; both of which are hereby incorporated by reference) were synthesized, kinased and annealed using standard molecular biology techniques (Sambrook et al., 1989 *Molecular Cloning: A Laboratory Manual,* 2nd Ed, Cold Spring Harbor Laboratory Press, Cold Spring Harbor, N.Y.). The sequences of the oligonucleotides used is 5'-CTGATTTCCC CGAAATGACG-3' (SEQ. ID NO. 1) and 5'-CGTCATTTCG GGGAAATCAT-3' (SEQ. ID NO. 2). The double stranded oligonucleotides were cloned into a Sma I site of pTKLuc. Plasmid pTKLuc contains a promoter sequence from −35 to +10 of the herpes simplex virus thymidine kinase gene (McKnight et al., 1982 *Science,* 217:316–324) upstream of the firefly luciferase gene found in pZLuc (Schadlow, et al., 1992 *Mol. Biol Cell* 3:941–951). The ligated DNA was used to transform *E. coli* using DH5$\alpha$ competent cells (Gibco/BRL, Gaithersburg, Md.). DNA obtained from the transformed colonies was analyzed by restriction digest analysis and the orientation and number of copies of SBE oligonucleotides found in each of the transformants was confirmed by sequencing through the insert using a sequencing kit (US Biochemical, Cleveland, Ohio). Clone AH32 was found to contain 3 copies of the SBE inserted in the same orientation and was used for further studies with a human fibroblast cell line (WI-38 VA13 subline 2RA; ATCC No. CCL 75.1). Cells transfected with the AH32 showed a 6–10 fold increase in the luciferase activity after 6 h of treatment with IFN-$\alpha$ or IFN-$\gamma$.

Primers ROBR 35 (5'-TTGGAGGACT ATGGGTGTC-3') (SEQ. ID NO. 3) and ROBR 37 (5'- CTACTGGAAT GGAACCTGG-3') (SEQ. ID NO. 4) were used to obtain the full length coding sequence for the rat OB-R, (approximately 3.7 kb in size) by the PCR using rat hypothalamic cDNA as the template. Long PCR produced the full length fragments by a modified method of Barnes (Barnes, 1994, *Proc. Natl. Acad. Sci.* 91:2216–2220, which is hereby incorporated by reference). For the long PCR reactions, Taq Extender (Stratagene, La Jolla, Calif.) and the Expand Long Template PCR System (Boehringer Mannheim, Indianapolis, Ind.) were used in combination. The standard PCR reaction mix, in a final volume of 20 $\mu$l, consisted of 40 ng of template (rat cDNA), 200 ng of primers, 500 mM dNTPs, 1×Buffer 3 from the Expand kit, and 0.2 ml of the Expand kit enzyme mix. Reactants were assembled in thin walled reaction tubes. The amplification protocol was 1 cycle of 92° C. for 30 sec., followed by 35 cycles at 92° C. for 30 sec., 54° C. for 1 min. and 68° C. for 5 min. using a Perkin Elmer 480 Thermal Cycler.

The DNA sequence of the full length products was determined using ABI PRISM Dye terminator cycle sequencing with AmpliTaq DNA polymerase, FS (Perkin Elmer, Foster City), and a number of PCR induced errors were detected. To eliminate these PCR induced mutations, restriction fragments from clones containing the correct DNA sequence were assembled. Three different restriction fragments were used to construct a full length clone derived from fa/fa hypothalamic cDNA, with a C at nucleotide 880. The expression construct was obtained by ligating a fragment from a hind III polylinker site to a Nde I site at nucleotide 502, a fragment from the Nde I site at 502 to a Sac I site at 1522, and a fragment from the Sac I site at 1522 to a Xba I polylinker site into the Hind III and Xba I sites of pcDNA 3 (Invitrogen, San Diego, Calif.). The wild type (lean) clone, with an A at nucleotide 880, was constructed by replacing the Nde I by Sac I fragment from 502 to 1522 with a fragment derived from lean hypothalamic cDNA.

pCH110, a vector expressing β-galactosidase under control of the SV40 early promoter (Hall et al., 1983, *J Mol Appl Gen* 2:101–109), was obtained from Pharmacia Biotech, Inc. (Piscataway, N.J.).

A fragment of the human Ob receptor cDNA, nucleotides 141–3770, containing the entire coding region was obtained using PCR and subcloned into pCMV4 (Andersson, S. 1989 *J Biol. Chem.* 264:8222–8229) a gift of D. W. Russell.

EXAMPLE 2

Cell Culture

GT1–7 cells, a mouse hypothalamic cell line, a gift of P. L. Mellon (Liposits et al., 1991 *Endocrinology* 129:1575–1583) were maintained in Dulbecco-modified Eagle Medium (DMEM) (Gibco/BRL, Gaithersburg, Md.), 10% bovine calf serum, 50 μg/ml streptomycin, and 50 U/ml penicillin (growth medium) at 37° C. in an atmosphere of 95% air, 5% $CO_2$. Cells were seeded at approximately $4 \times 10^4/cm^2$ and passaged before confluence.

EXAMPLE 3

Transfection of GT1–7 Cells 18 hours before transfection, cells were plated at $3.5 \times 10^5$ cells per 35 mm tissue culture dish. The plasmids AH32, appropriate Ob-r plasmid and pCH110 were introduced into cells using liposome-mediated transfection. Specifically, 300 ng of each plasmid was added to 200 μl of Optimem™ (Gibco/BRL, Gaithersburg, Md.). 10 μg of Lipofectamine™ (Gibco/BRL, Gaithersburg, Md.) was added to a second 200 μl volume of Optimem™. The two solutions were mixed, incubated at room temperature for 30 minutes and adjusted to 600 μl with Optimem™. Cells were washed twice with phosphate buffered saline. The DNA-liposome complex was applied to cells. Cells were incubated for 6 hours at which time 2 ml of growth medium was added to cells. 16 hours later, the transfection mixture was removed and 2 ml fresh growth medium was added.

EXAMPLE 4

Luciferase Assay

Approximately 24 hours after transfection, various amounts of recombinant human leptin were added to cells. Cells were then incubated for 24 hours. Cell culture medium was removed and cells were washed promptly with 2 ml of ice-cold calcium and magnesium-free phosphate buffered saline. Cells were then prepared for assay with 150 μl Promega reporter lysis reagent (Promega, Madison, Wis.) according to the manufacturer's protocol. 20 μl of cell lysates was then assayed for luciferase activity using a Dynatech ML 3000 luminometer (Dynatech, Chantilly, Va.) using cycle mode after initiating the reaction with 100 μl of Promega luciferase assay reagent. The β-galactosidase activity in 50 μl of each cell lysate was determined using a β-galactosidase assay (Promega, Madison, Wis.). Results were normalized by dividing the relative light units obtained for each sample by the β-galactosidase activity.

What is claimed is:

1. A method for determining if a leptin receptor binding compound is present in a sample comprising:
   contacting the sample with a cell which comprises
   a) nucleic acids comprising a promoter region, said promoter region comprising a promoter and at least one leptin response element wherein said response element is an IRF-1 -derived gamma-interferon activation sequence and wherein said promoter region is operatively linked to a reporter gene; and
   b) nucleic acids encoding a leptin receptor; and
   determining if transcription of the reporter gene occurs.

2. A method according to claim 1 wherein the IRF-1 derived gamma interferon activation sequence is CTG ATT TCC CCG AAA TGA CG (SEQ. ID NO. 1).

3. A method according to claim 2 wherein the promoter region comprises a plurality of leptin response elements.

4. A method according to claim 3 wherein the promoter region comprises at least three IRF-1 derived gamma-interferon activated sequences.

5. A method according to claim 2 wherein the leptin receptor is a recombinant leptin receptor.

6. A method according to claim 5 wherein the leptin receptor is human or rodent.

7. A method according to claim 6 wherein the nucleic acid encoding the leptin receptor comprises a sequence selected from the group of sequences consisting of those in FIGS. 3, 4 and 5.

8. A method according to claim 7 wherein the transcription of the reporter gene occurs in proportion to the amount of leptin receptor binding compound present.

9. A method for quantifying the amount of a leptin-receptor binding compound present in a sample comprising:
   contacting the sample with a cell which has been transfected with
   a) nucleic acids comprising a promoter region, said promoter region comprising a promoter and at least one leptin response element wherein said response element is an IRF-1-derived gamma-interferon activation sequence and wherein said promoter region is operatively linked to a reporter gene; and
   b) nucleic acids encoding a leptin receptor; and
   determining the amount of transcription of the reporter gene that occurs.

10. A method for determining the leptin binding ability of a putative leptin receptor comprising:
   providing a cell which expresses the putative leptin receptor, said cell also comprising nucleic acids comprising a promoter region, said promoter region comprising a promoter and at least one leptin response element wherein said response element is an IRF-1-derived gamma-interferon activation sequence, and wherein said promoter region is operatively linked to a reporter gene; and contacting the cell with leptin.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear    (ii) MOLECULE TYPE: Other    (xi) SEQUENCE DESCRIPTION: SEQ ID NO:1:

CTGATTTCCC CGAAATGACG      20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear    (ii) MOLECULE TYPE: Other    (xi) SEQUENCE DESCRIPTION: SEQ ID NO:2:

CGTCATTTCG GGAAATCAT      20

(2) INFORMATION FOR SEQ ID NO:3:

(i) SEQUENCE CHARACTERISTICS:
      (A) LENGTH: 19 base pairs (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:3:

TTGGAGGACT ATGGGTGTC                                                19

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:4:

CTACTGGAAT GGAACCTGG                                                19

(2) INFORMATION FOR SEQ ID NO:5:

(i) SEQUENCE CHARACTERISTICS:
        (A) LENGTH: 3650 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:5:

TGGGGCAATT GGGCTGACCT TTCTTATGCT GGGATGTGCC TTGGAGGACT ATGGGTGTCT     60

ATCTCTGAAG TAAGATGACG TGTCAGAAAT CTATGTGGT TTTGTTACAC TGGGAATTTC    120

TGTATGTGAT AACTGCACTT AACCTGGCCT ATCCAACCTC TCCCTGGAGA TTTAAGCTGT   180

TTTGTGCGCC ACCGAGTACA ACTGATGACT CCTTTCTCTC TCCTGCTGGA GTCCCAAACA   240

ATACTTCGTC TTTGAAGGGG GCTTCTGAAG CACTTGTTGA AGCTAAATTT AATTCAACTG   300

GTATCTACGT TTCTGAGTTA TCCAAAACCA TTTTCCACTG TTGCTTTGGG AATGAGCAAG   360

GTCAAAACTG CTCCGCACTC ACAGGCAACA CTGAAGGGAA GACGCTGGCT TCAGTGGTGA   420

AGCCTTTAGT TTTCCGCCAA CTAGGTGTAA ACTGGGACAT AGAGTGCTGG ATGAAAGGGG   480

ACTTGACATT ATTCATCTGT CATATGGAAC CATTACTTAA GAACCCCTTC AAGAATTATG   540

ACTCTAAGGT TCACCTTTTA TATGATCTGC CTGAAGTTAT AGATGATTTG CCTCTGCCCC   600

CACTGAAAGA CAGCTTTCAG ACTGTCCAGT GCAACTGCAG TGTTCGGGAA TGCAATGTC    660

ATGTACCAGT ACCCAGAGCC AAAGTCAACT ACGCTCTTCT GATGTATTTA GAAATCACAT   720

CTGCTGGTGT GAGTTTTCAG TCACCTCTAA TGTCACTGCA GCCCATGCTT GTTGTGAAGC   780

CCGATCCACC GCTGGGTTTG CGTATGGAAG TCACAGATGA TGGTAATTTA AAGATTTCAT   840

GGGACAGCCA AACAAAAGCA CCATTTCCAC TTCAATATCA GGTGAAATAT TTAGAGAATT   900

CTACAATCGT AAGAGAGGCT GCTGAAATCG TCTCGGATAC ATCTCTGCTG GTAGACAGCG   960

TGCTTCCTGG GTCTTCATAC GAGGTCCAGG TGAGGAGCAA GAGACTGGAT GGCTCAGGAG  1020

TCTGGAGTGA CTGGAGTTTA CCTCAACTCT TTACCACACA AGATGTCATG TATTTTCCAC  1080

CCAAAATTCT GACGAGTGTT GGATCCAATG CTTCCTTTTG CTGCATCTAC AAAAATGAGA  1140

ACCAGACTAT CTCCTCAAAA CAAATAGTTT GGTGGATGAA TCTAGCCGAG AAGATCCCCG  1200

AGACACAGTA CAACACTGTG AGTGACCACA TTAGCAAAGT CACTTTCTCC AACCTGAAAG  1260

-continued

```
CCACCAGACC TCGAGGGAAG TTTACCTATG ATGCAGTGTA CTGCTGCAAT GAGCAGGCAT    1320
GCCATCACCG CTACGCTGAA TTATATGTGA TCGATGTCAA TATCAATATA TCATGTGAAA    1380
CTGACGGGTA CTTAACTAAA ATGACTTGCA GATGGTCACC CAGCACAATC CAATCACTAG    1440
TGGGAAGCAC TGTGCAGTTG AGGTATCACA GGCGCAGCCT GTACTGTCCC GATAATCCAT    1500
CTATTCGTCC TACATCAGAG CTCAAAAACT GCGTCTTACA GACAGATGGC TTTTATGAAT    1560
GTGTTTTCCA GCCAATCTTT CTATTATCTG GCTATACAAT GTGGATCAGG ATCAACCATT    1620
CTTTAGGTTC ACTTGACTCT CCACCAACGT GTGTCCTTCC TGACTCCGTA GTAAAACCAC    1680
TACCTCCATC TAATGTAAAA GCAGAGATTA CTATAAACAC TGGATTATTG AAAGTATCTT    1740
GGGAAAAGCC AGTCTTTCCA GAGAATAACC TTCAGTTCCA GATTCGTATG GCTTAAATG    1800
GAAAAGAAAT ACAATGGAAG ACACACGAGG TATTCGATGC AAAATCAAAA TCGGCCAGCC    1860
TGCCAGTGTC AGATCTCTGT GCGGTCTATG TGGTACAGGT TCGCTGCCGG CGGTTGGATG    1920
GACTAGGGTA TTGGAGTAAT TGGAGCAGTC CAGCCTACAC TCTTGTCATG GATGTAAAAG    1980
TTCCTATGAG AGGGCCTGAA TTCTGGAGAA TAATGGATGG GGATATTACT AAAAAGGAGA    2040
GAAATGTCAC CTTGCTTTGG AAGCCACTGA TGAAAAATGA CTCACTGTGT AGTGTGAGGA    2100
GGTATGTGGT GAAGCATCGT ACTGCCCACA ATGGGACATG GTCACAAGAT GTGGGAAATC    2160
AGACCAATCT CACTTTCCTG TGGGCAGAAT CAGCACACAC TGTTACAGTT CTGGCCATCA    2220
ATTCCATCGG TGCCTCCCTT GTGAATTTTA ACCTTACGTT CTCATGGCCC ATGAGTAAAG    2280
TGAATGCTGT GCAGTCACTC AGTGCTTATC CCCTGAGCAG CAGCTGCGTC ATCCTTTCCT    2340
GGACACTGTC ACCTAATGAT TATAGTCTGT TATATCTGGT TATTGAATGG AAGAACCTTA    2400
ATGATGATGA TGGAATGAAG TGGCTTAGAA TCCCTTCGAA TGTTAACAAG TATTATATCC    2460
ATGATAATTT TATTCCTATC GAGAAATATC AGTTTAGTCT TTACCCAGTA TTTATGGAAG    2520
GAGTTGGAAA ACCAAAGATA ATTAATGGTT TCACCAAAGA TGATATCGCC AAACAGCAAA    2580
ATGATGCAGG GCTGTATGTC ATTGTACCGA TAATTATTTC CTCTTGTGTC CTGCTGCTCG    2640
GAACACTGTT AATTTCACAC CAGAGAATGA AAAAGTTGTT TTGGGACGAT GTTCCAAACC    2700
CCAAGAATTG TTCCTGGGCA CAAGGACTTA ATTTCCAAAA GCCTGAAACA TTTGAGCATC    2760
TTTTTACCAA GCATGCAGAA TCAGTGATAT TTGGTCCTCT TCTTCTGGAG CCTGAACCAG    2820
TTTCAGAAGA AATCAGTGTC GATACAGCTT GGAAAAATAA AGATGAGATG GTACCAGCAG    2880
CTATGGTCTC ACTTCTTTTG ACCACTCCAG ATTCCACAAG GGGTTCTATT TGTATCAGTG    2940
ACCAGTGTAA CAGTGCTAAC TTCTCTGGGG CTCAGAGCAC CCAGGGAACC TGTGAGGATG    3000
AGTGTCAGAG TCAACCCTCA GTTAAATATG CAACGCTGGT CAGCAACGTG AAAACAGTGG    3060
AAACTGATGA AGAGCAAGGG GCTATACATA GTTCTGTCAG CCAGTGCATC GCCAGGAAAC    3120
ATTCCCCACT GAGACAGTCT TTTTCTAGCA ACTCCTGGGA GATAGAGGCC CAGGCATTTT    3180
TCCTTTTATC AGATCATCCA CCCAATGTGA TTTCACCACA ACTTTCATTC TCAGGGTTGG    3240
ATGAGCTTTT GGAACTGGAG GGAAATTTTC CTGAAGAAAA TCACGGGGAA AAATCTGTGT    3300
ATTATCTAGG AGTCTCCTCA GGAAACAAAA GAGAGAATGA TATGCTTTTG ACTGATGAGG    3360
CAGGGGTATT GTGCCCATTC CCAGCTCACT GTCTGTTCAG TGACATCAGA ATCCTCCAGG    3420
AGAGTTGTTC ACACTTTGTA GAAAATAATT TGAATTTAGG GACCTCTGGT AAGAACTTTG    3480
TACCTTACAT GCCCCAGTTT CAATCCTGTT CCACTCACAG TCATAAGATA ATAGAAAATA    3540
AGATGTGTGA CTTAACTGTG TAATCTTGTC CAAAAACTTC CAGGTTCCAT TCCAGTAGAG    3600
TGTGTCATGT ATAATATGTT CTTTTATAGT TGTGGGTGGG AGAGAAAGCC              3650
```

(2) INFORMATION FOR SEQ ID NO:6:

(i) SEQUENCE CHARACTERISTICS:
        (A) LENGTH: 3629 base pairs
        (B) TYPE: nucleic acid
        (C) STRANDEDNESS: single
        (D) TOPOLOGY: linear     (ii) MOLECULE TYPE: Other     (xi) SEQUENCE DESCRIPTION: SEQ ID NO:6:

```
CTTATGCTGG GATGTGCCTT AGAGGATTAT GGGTGTACTT CTCTGAAGTA AGATGATTTG      60

TCAAAAATTC TGTGTGGTTT TGTTACATTG GGAATTTATT TATGTGATAA CTGCGTTTAA     120

CTTGTCATAT CCAATTACTC CTTGGAGATT TAAGTTGTCT TGCATGCCAC CAAATTCAAC     180

CTATGACTAC TTCCTTTTGC CTGCTGGACT CTCAAAGAAT ACTTCAAATT CGAATGGACA     240

TTATGAGACA GCTGTTGAAC CTAAGTTTAA TTCAAGTGGT ACTCACTTTT CTAACTTATC     300

CAAAACAACT TTCCACTGTT GCTTTCGGAG TGAGCAAGAT AGAAACTGCT CCTTATGTGC     360

AGACAACATT GAAGGAAAGA CATTTGTTTC AACAGTAAAT TCTTTAGTTT TTCAACAAAT     420

AGATGCAAAC TGGAACATAC AGTGCTGGCT AAAAGGAGAC TTAAAATTAT TCATCTGTTA     480

TGTGGAGTCA TTATTTAAGA ATCTATTCAG GAATTATAAC TATAAGGTCC ATCTTTTATA     540

TGTTCTGCCT GAAGTGTTAG AAGATTCACC TCTGGTTCCC CAAAAAGGCA GTTTTCAGAT     600

GGTTCACTGC AATTGCAGTG TTCATGAATG TTGTGAATGT CTTGTGCCTG TGCCAACAGC     660

CAAACTCAAC GACACTCTCC TTATGTGTTT GAAAATCACA TCTGGTGGAG TAATTTTCCA     720

GTCACCTCTA ATGTCAGTTC AGCCCATAAA TATGGTGAAG CCTGATCCAC CATTAGGTTT     780

GCATATGGAA ATCACAGATG ATGGTAATTT AAAGATTTCT TGGTCCAGCC CACCATTGGT     840

ACCATTTCCA CTTCAATATC AAGTGAAATA TTCAGAGAAT CTACAACAG TTATCAGAGA     900

AGCTGACAAG ATTGTCTCAG CTACATCCCT GCTAGTAGAC AGTATACTTC CTGGGTCTTC     960

GTATGAGGTT CAGGTGAGGG GCAAGAGACT GGATGGCCCA GGAATCTGGA GTGACTGGAG    1020

TACTCCTCGT GTCTTTACCA CACAAGATGT CATATACTTT CCACCTAAAA TTCTGACAAG    1080

TGTTGGGTCT AATGTTTCTT TCACTGCAT CTATAAGAAG GAAAACAAGA TTGTTCCCTC     1140

AAAAGAGATT GTTTGGTGGA TGAATTTAGC TGAGAAAATT CCTCAAAGCC AGTATGATGT    1200

TGTGAGTGAT CATGTTAGCA AAGTTACTTT TTTCAATCTG AATGAAACCA AACCTCGAGG    1260

AAAGTTTACC TATGATGCAG TGTACTGCTG CAATGAACAT GAATGCCATC ATCGCTATGC    1320

TGAATTATAT GTGATTGATG TCAATATCAA TATCTCATGT GAAACTGATG GGTACTTAAC    1380

TAAAATGACT TGCAGATGGT CAACCAGTAC AATCCAGTCA CTTGCGGAAA GCACTTTGCA    1440

ATTGAGGTAT CATAGGAGCA GCCTTTACTG TTCTGATATT CCATCTATTC ATCCCATATC    1500

TGAGCCCAAA GATTGCTATT GCAGAGTGA TGGTTTTTAT GAATGCATTT TCCAGCCAAT     1560

CTTCCTATTA TCTGGCTACA CAATGTGGAT TAGGATCAAT CACTCTCTAG GTTCACTTGA    1620

CTCTCCACCA ACATGTGTCC TTCCTGATTC TGTGGTGAAG CCACTGCCTC CATCCAGTGT    1680

GAAAGCAGAA ATTACTATAA ACATTGGATT ATTGAAAATA TCTTGGGAAA AGCCAGTCTT    1740

TCCAGAGAAT AACCTTCAAT TCCAGATTCG CTATGGTTTA AGTGGAAAAG AAGTACAATG    1800

GAAGATGTAT GAGGTTTATG ATGCAAAATC AAAATCTGTC AGTCTCCCAG TTCCAGACTT    1860

GTGTGCAGTC TATGCTGTTC AGGTGCGCTG TAAGAGGCTA GATGGACTGG GATATTGGAG    1920

TAATTGGAGC AATCCAGCCT ACACAGTTGT CATGGATATA AAAGTTCCTA TGAGAGGACC    1980

TGAATTTTGG AGAATAATTA ATGGAGATAC TATGAAAAAG GAGAAAAATG TCACTTTACT    2040
```

```
TTGGAAGCCC CTGATGAAAA ATGACTCATT GTGCAGTGTT CAGAGATATG TGATAAACCA    2100

TCATACTTCC TGCAATGGAA CATGGTCAGA AGATGTGGGA AATCACACGA AATTCACTTT    2160

CCTGTGGACA GAGCAAGCAC ATACTGTTAC GGTTCTGGCC ATCAATTCAA TTGGTGCTTC    2220

TGTTGCAAAT TTTAATTTAA CCTTTTCATG GCCTATGAGC AAAGTAAATA TCGTGCAGTC    2280

ACTCAGTGCT TATCCTTTAA ACAGCAGTTG TGTGATTGTT TCCTGGATAC TATCACCCAG    2340

TGATTACAAG CTAATGTATT TTATTATTGA GTGGAAAAAT CTTAATGAAG ATGGTGAAAT    2400

AAAATGGCTT AGAATCTCTT CATCTGTTAA GAAGTATTAT ATCCATGATC ATTTTATCCC    2460

CATTGAGAAG TACCAGTTCA GTCTTTACCC AATATTTATG GAAGGAGTGG GAAAACCAAA    2520

GATAATTAAT AGTTTCACTC AAGATGATAT TGAAAAACAC CAGAGTGATG CAGGTTTATA    2580

TGTAATTGTG CCAGTAATTA TTTCCTCTTC CATCTTATTG CTTGGAACAT TATTAATATC    2640

ACACCAAAGA ATGAAAAAGC TATTTTGGGA AGATGTTCCG AACCCCAAGA ATTGTTCCTG    2700

GGCACAAGGA CTTAATTTTC AGAAGCCAGA AACGTTTGAG CATCTTTTTA TCAAGCATAC    2760

AGCATCAGTG ACATGTGGTC CTCTTCTTTT GGAGCCTGAA ACAATTTCAG AAGATATCAG    2820

TGTTGATACA TCATGGAAAA ATAAAGATGA GATGATGCCA ACAACTGTGG TCTCTCTACT    2880

TTCAACAACA GATCTTGAAA AGGGTTCTGT TTGTATTAGT GACCAGTTCA ACAGTGTTAA    2940

CTTCTCTGAG GCTGAGGGTA CTGAGGTAAC CTATGAGGCC GAAAGCCAGA GACAACCCTT    3000

TGTTAAATAC GCCACGCTGA TCAGCAACTC TAAACCAAGT GAAACTGGTG AAGAACAAGG    3060

GCTTATAAAT AGTTCAGTCA CCAAGTGCTT CTCTAGCAAA AATTCTCCGT TGAAGGATTC    3120

TTTCTCTAAT AGCTCATGGG AGATAGAGGC CCAGGCATTT TTTATATTAT CAGATCAGCA    3180

TCCCAACATA ATTTCACCAC ACCTCACATT CTCAGAAGGA TTGGATGAAC TTTTGAAATT    3240

GGAGGGAAAT TTCCCTGAAG AAAATAATGA TAAAAAGTCT ATCTATTATT TAGGGGTCAC    3300

CTCAATCAAA AAGAGAGAGA GTGGTGTGCT TTTGACTGAC AAGTCAAGGG TATCGTGCCC    3360

ATTCCCAGCC CCCTGTTTAT TCACGGACAT CAGAGTTCTC CAGGACAGTT GCTCACACTT    3420

TGTAGAAAAT AATATCAACT TAGGAACTTC TAGTAAGAAG ACTTTTGCAT CTTACATGCC    3480

TCAATTCCAA ACTTGTTCTA CTCAGACTCA TAAGATCATG GAAAACAAGA TGTGTGACCT    3540

AACTGTGTAA TTTCACTGAA GAAACCTTCA GATTTGTGTT ATAATGGGTA ATATAAAGTG    3600

TAATAGATTA TAGTTGTGGG TGGGAGAGA                                      3629

(2) INFORMATION FOR SEQ ID NO:7:

(i) SEQUENCE CHARACTERISTICS:
        (A) LENGTH: 3650 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:7:

TGGGGCAATT GGGCTGACCT TTCTTATGCT GGGATGTGCC TTGGAGGACT ATGGGTGTCT      60

ATCTCTGAAG TAAGATGACG TGTCAGAAAT TCTATGTGGT TTTGTTACAC TGGGAATTTC     120

TGTATGTGAT AACTGCACTT AACCTGGCCT ATCCAACCTC TCCCTGGAGA TTTAAGCTGT     180

TTTGTGCGCC ACCGAGTACA ACTGATGACT CCTTTCTCTC TCCTGCTGGA GTCCCAAACA     240

ATACTTCGTC TTTGAAGGGG GCTTCTGAAG CACTTGTTGA AGCTAAATTT AATTCAACTG     300

GTATCTACGT TTCTGAGTTA TCCAAAACCA TTTTCCACTG TTGCTTTGGG AATGAGCAAG     360
```

-continued

```
GTCAAAACTG CTCCGCACTC ACAGGCAACA CTGAAGGGAA GACGCTGGCT TCAGTGGTGA    420
AGCCTTTAGT TTTCCGCCAA CTAGGTGTAA ACTGGACATA AGAGTGCTGG ATGAAAGGGG    480
ACTTGACATT ATTCATCTGT CATATGGAAC CATTACTTAA GAACCCCTTC AAGAATTATG    540
ACTCTAAGGT TCACCTTTTA TATGATCTGC CTGAAGTTAT AGATGATTTG CCTCTGCCCC    600
CACTGAAAGA CAGCTTTCAG ACTGTCCAGT GCAACTGCAG TGTTCGGGAA TGCGAATGTC    660
ATGTACCAGT ACCCAGAGCC AAAGTCAACT ACGCTCTTCT GATGTATTTA GAAATCACAT    720
CTGCTGGTGT GAGTTTTCAG TCACCTCTAA TGTCACTGCA GCCCATGCTT GTTGTGAAGC    780
CCGATCCACC GCTGGGTTTG CGTATGGAAG TCACAGATGA TGGTAATTTA AAGATTTCAT    840
GGGACAGCCA AACAAAAGCA CCATTTCCAC TTCAATATCC GGTGAAATAT TTAGAGAATT    900
CTACAATCGT AAGAGAGGCT GCTGAAATCG TCTCGGATAC ATCTCTGCTG GTAGACAGCG    960
TGCTTCCTGG GTCTTCATAC GAGGTCCAGG TGAGGAGCAA GAGACTGGAT GGCTCAGGAG   1020
TCTGGAGTGA CTGGAGTTTA CCTCAACTCT TTACCACACA AGATGTCATG TATTTTCCAC   1080
CCAAAATTCT GACGAGTGTT GGATCCAATG CTTCCTTTTG CTGCATCTAC AAAAATGAGA   1140
ACCAGACTAT CTCCTCAAAA CAAATAGTTT GGTGGATGAA TCTAGCCGAG AAGATCCCCG   1200
AGACACAGTA CAACACTGTG AGTGACCACA TTAGCAAAGT CACTTTCTCC AACCTGAAAG   1260
CCACCAGACC TCGAGGGAAG TTTACCTATG ATGCAGTGTA CTGCTGCAAT GAGCAGGCAT   1320
GCCATCACCG CTACGCTGAA TTATATGTGA TCGATGTCAA TATCAATATA TCATGTGAAA   1380
CTGACGGGTA CTTAACTAAA ATGACTTGCA GATGGTCACC CAGCACAATC CAATCACTAG   1440
TGGGAAGCAC TGTGCAGTTG AGGTATCACA GGCGCAGCCT GTACTGTCCC GATAATCCAT   1500
CTATTCGTCC TACATCAGAG CTCAAAAACT GCGTCTTACA GACAGATGGC TTTTATGAAT   1560
GTGTTTTCCA GCCAATCTTT CTATTATCTG GCTATACAAT GTGGATCAGG ATCAACCATT   1620
CTTTAGGTTC ACTTGACTCT CCACCAACGT GTGTCCTTCC TGACTCCGTA GTAAAACCAC   1680
TACCTCCATC TAATGTAAAA GCAGAGATTA CTATAAACAC TGGATTATTG AAAGTATCTT   1740
GGGAAAAGCC AGTCTTTCCA GAGAATAACC TTCAGTTCCA GATTCGATAT GGCTTAAATG   1800
GAAAAGAAAT ACAATGGAAG ACACACGAGG TATTCGATGC AAAATCAAAA TCGGCCAGCC   1860
TGCCAGTGTC AGATCTCTGT GCGGTCTATG TGGTACAGGT TCGCTGCCGG CGGTTGGATG   1920
GACTAGGGTA TTGGAGTAAT TGGAGCAGTC CAGCCTACAC TCTTGTCATG GATGTAAAAG   1980
TTCCTATGAG AGGGCCTGAA TTCTGGAGAA TAATGGATGG GGATATTACT AAAAAGGAGA   2040
GAAATGTCAC CTTGCTTTGG AAGCCACTGA TGAAAAATGA CTCACTGTGT AGTGTGAGGA   2100
GGTATGTGGT GAAGCATCGT ACTGCCCACA ATGGGACATG GTCACAAGAT GTGGGAAATC   2160
AGACCAATCT CACTTTCCTG TGGGCAGAAT CAGCACACAC TGTTACAGTT CTGGCCATCA   2220
ATTCCATCGG TGCCTCCCTT GTGAATTTTA ACCTTACGTT CTCATGGCCC ATGAGTAAAG   2280
TGAATGCTGT GCAGTCACTC AGTGCTTATC CCCTGAGCAG CAGCTGCGTC ATCCTTTCCT   2340
GGACACTGTC ACCTAATGAT TATAGTCTGT TATATCTGGT TATTGAATGG AAGAACCTTA   2400
ATGATGATGA TGGAATGAAG TGGCTTAGAA TCCCTTCGAA TGTTAACAAG TATTATATCC   2460
ATGATAATTT TATTCCTATC GAGAAATATC AGTTTAGTCT TTACCCAGTA TTTATGGAAG   2520
GAGTTGGAAA ACCAAAGATA ATTAATGGTT TCACCAAAGA TGATATCGCC AAACAGCAAA   2580
ATGATGCAGG GCTGTATGTC ATTGTACCGA TAATTATTTC CTCTTGTGTC CTGCTGCTCG   2640
GAACACTGTT AATTTCACAC CAGAGAATGA AAAAGTTGTT TTGGGACGAT GTTCCAAACC   2700
CCAAGAATTG TTCCTGGGCA CAAGGACTTA ATTTCCAAAA GCCTGAAACA TTTGAGCATC   2760
```

-continued

```
TTTTTACCAA GCATGCAGAA TCAGTGATAT TTGGTCCTCT TCTTCTGGAG CCTGAACCAG    2820

TTTCAGAAGA AATCAGTGTC GATACAGCTT GGAAAAATAA AGATGAGATG GTACCAGCAG    2880

CTATGGTCTC ACTTCTTTTG ACCACTCCAG ATTCCACAAG GGGTTCTATT TGTATCAGTG    2940

ACCAGTGTAA CAGTGCTAAC TTCTCTGGGG CTCAGAGCAC CCAGGGAACC TGTGAGGATG    3000

AGTGTCAGAG TCAACCCTCA GTTAAATATG CAACGCTGGT CAGCAACGTG AAAACAGTGG    3060

AAACTGATGA AGAGCAAGGG GCTATACATA GTTCTGTCAG CCAGTGCATC GCCAGGAAAC    3120

ATTCCCCACT GAGACAGTCT TTTTCTAGCA ACTCCTGGGA GATAGAGGCC CAGGCATTTT    3180

TCCTTTTATC AGATCATCCA CCCAATGTGA TTTCACCACA ACTTTCATTC TCAGGGTTGG    3240

ATGAGCTTTT GGAACTGGAG GGAAATTTTC CTGAAGAAAA TCACGGGGAA AAATCTGTGT    3300

ATTATCTAGG AGTCTCCTCA GGAAACAAAA GAGAGAATGA TATGCTTTTG ACTGATGAGG    3360

CAGGGGTATT GTGCCCATTC CCAGCTCACT GTCTGTTCAG TGACATCAGA ATCCTCCAGG    3420

AGAGTTGTTC ACACTTTGTA GAAAATAATT TGAATTTAGG GACCTCTGGT AAGAACTTTG    3480

TACCTTACAT GCCCCAGTTT CAATCCTGTT CCACTCACAG TCATAAGATA ATAGAAAATA    3540

AGATGTGTGA CTTAACTGTG TAATCTTGTC CAAAAACTTC CAGGTTCCAT TCCAGTAGAG    3600

TGTGTCATGT ATAATATGTT CTTTTATAGT TGTGGGTGGG AGAGAAAGCC              3650
```